US009566291B2

(12) United States Patent
Boehm et al.

(10) Patent No.: US 9,566,291 B2
(45) Date of Patent: *Feb. 14, 2017

(54) NUTRITIONAL COMPOSITION COMPRISING INDIGESTIBLE OLIGOSACCHARIDES

(75) Inventors: Günther Boehm, Echzell (DE); Laura M'Rabet, Amersfoort (NL); Bernd Stahl, Rosbach-Rodheim (DE); Johan Garssen, Nieuwegein (NL)

(73) Assignee: N.V. Nutricia, Zoetermeer (NL)

( * ) Notice: Subject to any disclaimer, the term of this patent is extended or adjusted under 35 U.S.C. 154(b) by 1627 days.

This patent is subject to a terminal disclaimer.

(21) Appl. No.: 11/574,180

(22) PCT Filed: Aug. 24, 2005

(86) PCT No.: PCT/NL2005/000611
§ 371 (c)(1),
(2), (4) Date: Jul. 10, 2007

(87) PCT Pub. No.: WO2006/022542
PCT Pub. Date: Mar. 2, 2006

(65) Prior Publication Data
US 2008/0124323 A1 May 29, 2008

(30) Foreign Application Priority Data
Aug. 24, 2004 (EP) .................................. 04077394

(51) Int. Cl.
| | | |
|---|---|---|
| A61K 31/715 | (2006.01) | |
| A61K 31/733 | (2006.01) | |
| A61K 39/42 | (2006.01) | |
| A61K 45/00 | (2006.01) | |
| A61P 11/00 | (2006.01) | |
| A61K 31/702 | (2006.01) | |
| A61K 31/202 | (2006.01) | |
| A61K 35/741 | (2015.01) | |

(52) U.S. Cl.
CPC ............. *A61K 31/702* (2013.01); *A23L 33/12* (2016.08); *A23L 33/21* (2016.08); *A23L 33/40* (2016.08); *A61K 31/202* (2013.01); *A61K 31/733* (2013.01); *A61K 35/741* (2013.01); *A61K 39/42* (2013.01); *A23V 2002/00* (2013.01); *A23Y 2300/29* (2013.01)

(58) Field of Classification Search
CPC .. A61K 31/733; A61K 31/702; A61K 35/741; A61K 31/7016; A23L 1/296; A23L 1/308; A23L 1/3008
See application file for complete search history.

(56) References Cited

U.S. PATENT DOCUMENTS

| | | | |
|---|---|---|---|
| 4,661,345 A | 4/1987 | Tuomanen | |
| 4,800,078 A | 1/1989 | Prince et al. | |
| 4,919,961 A | 4/1990 | Lundblad | |
| 5,792,754 A | 8/1998 | Green et al. | |
| 5,902,617 A | 5/1999 | Pabst | |
| 5,922,344 A | 7/1999 | Hilty et al. | |
| 6,146,670 A | 11/2000 | Prieto et al. | |
| 6,863,918 B2 | 3/2005 | Bindels et al. ............... | 426/590 |
| 7,794,746 B2 | 9/2010 | Gibson et al. | |
| 2003/0022863 A1 | 1/2003 | Stahl et al. | |
| 2003/0072865 A1* | 4/2003 | Bindels et al. ............... | 426/601 |
| 2004/0029127 A1* | 2/2004 | Postaire et al. .................. | 435/6 |
| 2004/0062758 A1 | 4/2004 | Mayra-Makinen et al. ......................... | 424/93.45 |
| 2004/0072791 A1 | 4/2004 | Kunz et al. | |
| 2004/0131659 A1 | 7/2004 | Gibson et al. | |
| 2006/0018890 A1 | 1/2006 | Isolauri et al. | |
| 2008/0124323 A1 | 5/2008 | Boehm et al. | |

FOREIGN PATENT DOCUMENTS

| | | |
|---|---|---|
| AU | 766429 B2 | 10/2003 |
| DE | 198 36 339 A1 | 2/2000 |
| EP | 0 126 043 | 11/1984 |
| EP | 0 272 095 | 2/1989 |
| EP | 0 808 173 A | 11/1997 |
| EP | 0 756 828 B1 | 11/1998 |
| EP | 1 254 664 A2 | 11/2002 |
| GB | 1 573 995 | 9/1980 |
| NZ | 522916 A | 3/2004 |
| WO | WO-92/02817 | 2/1992 |
| WO | WO-96/13271 A1 | 5/1996 |
| WO | WO-96/31186 | 10/1996 |
| WO | WO-96/40169 | 12/1996 |

(Continued)

OTHER PUBLICATIONS

"Viral Upper Respiratory Infections" from The Galen Medical Group [online], [retrieved Aug. 9, 2010]. Retrieved from the internet http://www.galenmedical.com/downloads.ViralInfections824.pdf. Published May 24, 2006.*
Kayser, F.H. (1992) Changes iin the spectrum of organism causing respiratory tract infections: a review. Postgraduate Medical Journal, vol. 68, suppl 3, p. S17-S23.*
Downham, M.A.P.S., Scott, R., Sims, D.G., Webb, J.K.G., Gardner, P.S. (1976) Breast-feeding protects against respiratory syncytial virus infections. British Medical Journal, vol. 2, p. 274-276.*
Gibson, G.R., Rabiu, B., Rycroft, C.E., Rastall, R.A. (2004) "Trans-Galactooligosaccharides as Prebiotics" in the Handbook of Functional Dairy Products. Edited by Colette Shortt and John O'Brien. Published by CRC Press.*

(Continued)

*Primary Examiner* — Layla Berry
(74) *Attorney, Agent, or Firm* — Foley & Lardner LLP; Sunit Talapatra

(57) ABSTRACT

The present invention provides a method and composition for the treatment and/or prevention of respiratory tract infection and/or respiratory tract infection disease, said method comprising orally administering a composition to a mammal, said composition comprising a galactose containing indigestible oligosaccharide and at least 5 wt. % digestible galactose saccharide.

21 Claims, No Drawings

(56) References Cited

FOREIGN PATENT DOCUMENTS

| WO | WO-98/44917 A1 | 10/1998 |
| WO | WO-00/08948 | 2/2000 |
| WO | WO-00/42868 | 7/2000 |
| WO | WO 00/42868 | 7/2000 |
| WO | WO-01/41581 A1 | 6/2001 |
| WO | WO-01/97817 A1 | 12/2001 |
| WO | WO 02/02105 A1 | 1/2002 |
| WO | WO 03/026567 A2 | 4/2003 |
| WO | WO-03/028738 A2 | 4/2003 |
| WO | WO-2004/052121 A | 6/2004 |
| WO | WO 2006/018314 * | 2/2006 |
| WO | WO-2006/022542 A1 | 3/2006 |

OTHER PUBLICATIONS

Prentice, A. (1996) "Constituents of human milk" in the Food and Nutrition Bulletin [online], [Retrieved on Aug. 2, 2010]. Edited by Scrimshaw, N.S. Published by United Nations University Press. Retrieved from the internet: <http://www.unu.edu/unupress/food/8f174e/8F174E00.htm>.*
"Diagnosing RSV" from The RSV Info Center [online], [retrieved Aug. 11, 2010]. Retrieved from the internet http://www.rsvinfo.com/diagnosing/diagnosing.html. Published on Feb. 20, 1999.*
"Respiratory syncytial virus(RSV)" MedlinePlus Medical Encyclopedia [online], [retrieved Aug. 11, 2010]. Retrieved from the Internet http://www.nlm.nih.gov/medlineplus/ency/article/001564.htm. Published on Jun. 17, 2001.*
McIntosh, K. (1997) "Respiratory Syncytial Virus" in Viral Infections of Humans: Epidemiology and Control. Edited by Evans, A.S. and Kaslow, R.A. Published by Plenum Medical Book Company, p. 691-711.*
"Respiratory Syncytial Virus" from Drugs.com [online] Published online Jun. 3, 2009. Retrieved from the internet on Nov. 8, 2013 from <http://www.drugs.com/cg/respiratory-syncytial-virus.html>.*
"Infant Formulas (Systemic)" by Drugs.com [online] Retrieved on Mar. 10, 2014 from <http://www.drugs.com/mmx/enfamil-premature-formula.html>.*
Gibson, G.R., Rabiu, B., Rycroft, C.E., Rastall, R.A. (2003) "Trans-Galactooligosaccharides as Prebiotics" in Handbook of Functional Dairy Products. Edited by Colette Shortt and John O'Brien, published by CRC Press, p. 91-108.*
"Infant formulas" by MEDLINEplus Medical Encyclopedia [online] Published on Feb. 10, 2003. Retrieved on Feb. 28, 2014 from <http://www.nlm.nih.gov/medlineplus/ency/article/002447.htm>.*
Moro, G., Minoli, I., Mosca, M., Fanaro, S., Jelinek, J., Stahl, B., Boehm, G. (2002) Dosage-Related Bifidogenic Effects of Galacto- and Fructooligosaccharides in Formula-Fed Term Infants. Journal of Pediatric Gastroenterology and Nutrition, vol. 34, p. 291-295.*
Boehm, G., Jelinek, J., Stahl, B., van Laere, K., Knol, J., Fanaro, S., Moro, G., Vigi, V. (2004) Prebiotics in Infant Formulas. Journal of Clinical Gastroenterology, vol. 38, supp. 2, p. S76-S79.*
Link-Amster, H., Rochat, F., Saudan, K.Y., Mignot, O., Aeschlimann, J.M. (1994) Modulation of a specific humoral immune response and changes in intestinal flora mediated through fermented milk intake. FEMS Immunology and Medical Microbiology, vol. 10, p. 55-64.*
Schley, P.D., Field, C.J. (2002) The immune-enhancing effects of dietary fibres and prebiotics. British Journal of Nutrition, vol. 87, supp. 2, S221-S230.*
Lowry et al. (Infant Formulas—An update obtained from http://www.hini.org/HINI/infform.htm)—retrieved online Apr. 28, 2008.
Niness et al. The Journal of Nutrition 129:1402S-1406S, 1999.
Hemming et al. Clinical and Diagnostic Lab. Immunol. Sep. 2001 p. 859-863.
Taylor et al. Clin. Exp. Immunol 1992, vol. 90:357-362.
Sabchareon et al. Am J. Trop Med. Hyg 1991 vol. 45:297-308.
Boehm et al. Arch Dis Child Fetal Neonatal Ed. 2002; 86:F178-F181.
International Search Report (PCT/NL2005/000612) dated Jan. 20, 2006.
Mar. 31, 2007 Frank Fox Declaration Elix' or brochure 1996.
A. Prentice, "Constituents of human milk", Food and Nutrition Bulletin, vol. 17, No. 4 (1996).
A. Sinha et al, "Reduced Risk of Neonatal Respirator Infections Among Breasted Girls but Not Boys", Pediatrics, vol. 112, No. 4, 2003.
B. Anderson et al., "Inhibition of Attachment of Streptococcus pneumoniae and Haemophilus influenzae by Human Milk and Receptor Oligosaccharides", The Journal of Infectious Diseases, vol. 153, No. 2, (1986).
C.R. Pullen et al., "Breast-feeding and respirator syncytial virus infection", British Medical Journal, vol. 281 (1980).
D.S. Newburg et al., "Carbohydrates in Milks: Analysis, Quantities, and Significance" Handbook of Milk Composition, New York: Academic Press, 1995, Chapter 4.
Definition of Infection—American Heritage Dictionary (http://www.bartleby.com/61/70/10127000.html. Retrieved Jan. 21, 2009.
Definition of Infection—http://www.mercksource.com/pp/us/cns/cns_hl_dorlands_split.jsp?pg=/ppdocs/us/common/dorlands/dorland/four/000053439.html. Retrieved Jan. 21, 2009.
Definition of Infection—Online Medical Dictionary http://cancerweb.ncl.ac.uk/cgi-bin/omd?infection. Retrieved Jan. 21, 2009.
Definition of Infection—Stedman's Online Medical Dictionary (http://www.stedmans.com/section.cfm/45. Retrieved Jan. 21, 2009.
E. Birch et al, "A randomized controlled trial of long-chain polyunsaturated fatty acid supplementation of formula in term infants weaning at 6 wk of age", American Journal of Clinical Nutrition, vol. 75, No. 3, (2002).
E. Tuomanen et al., "Receptor Analogs and Monoclonal Antibodies that Inhibit Adherence to Bordetella Pertusis to Human Ciliated Respiratory Epithelian Cells", J. Exp. Med. vol. 168 (1988).
Elix' or (Milupa Friedrichsdorf Jun. 29, 1998).
Elix' or Galacto-oligosaccharides—A natural ingredient for functional foods.
Elix' or Galacto-oligosaccharides—for Innovative Foods.
Flexnews, "Friesland Foods Domo Further Expands Production Capacity", download Jan. 21, 2008 from http://www.flex=news.food.com/pages/8170/Friesland'friesland_foods_dome_furhter_expands_production_capacity.html.
Food and Nutrition Bulletin (The United Nations University Press) Dec. 1996, vol. 17, No. 4, (Constituents of Breast Milk and Protective Effect of Breast Milk against infection).
Gibson, et al., "Dietary Modulation of the Human Colonic Microbiota: Introducing the Concept of Prebiotic," J Nutr., Jun. 1995, vol. 125, No. 6, pp. 1401, 1405.
Hatakka, et al. "Effect of long Term Consumption of Probiotic Milk on Infections in Children Attending Day Care Centres: Double Blind, Randomised Trial" BMJ, Jun. 2, 2001, vol. 322, pp. 1-5.
J. Charlwood et al, "A Detailed Analysis of Neutral and Acidic Carbohydrates in Human Milk," Analytical Biochemistry, vol. 273, issue 2, 1999.
J.M. Saavedra et al., "Human studies with probiotics and prebiotics: clinical implications", British Journal of Nutrition, vol. 87, Suppl. 2 (2002).
M A P S Downham et al, "Breast-feeding protects against respiratory syncytial virus infections", British Medical Journal, vol. 2., 1976, pp. 274-276.
M. Rivero et al, "P1121 Effect of a New Infant Formulae Enriched Prebiotics, Probiotics, Nucleotides and LC-Pufa's on Infants Recovery after an Infection" [abstracts], Journal of Pediatric Gastroenterology and Nutrition, vol. 39, supplement 1, 2004.
S.E. Carlson, "N-Acetylneuraminic acid concentrations in human milk oligosaccharides and glycoproteins during lactation" American Journal of Clinical Nutrition, vol. 41, Apr. 1985, pp. 720-726.
Upper Respiratory Tract Infections—http://www.clevelandclinicmeded.com/medicalpubs/diseasemanagement/infectious-disease/upper-respiratory-tract-infection/. Retrieved Jan. 21, 2009.

(56) References Cited

OTHER PUBLICATIONS

Hatakka et al BMJ;322;1-5, 2001.
Definition of Infection—http://www.mercksource.com/pp/us/cns/cns_hl_dorlands_split.jsp?pg=/ppdocs/us/common/dorlands/dorland/four/000053439.htm. Retrieved Jan. 21, 2009.
Definition of Infection—Stedman's Online Medical Dictionary (http://www.stedmans.com/section.cfm/45.Retrieved Jan. 21, 2009.
Upper Respiratory Tract Infections—http://www.clevelandclinicmeded.com/medicalpubs/diseasemanagement/infectious-disease/upper-respiratory-tract-infection/, retrieved Jan. 21, 2009.
Devereux, H.M. et al., "Consumer Acceptability of Low Fat Foods Containing Inulin and Oligofructose", Journal of Food Science, 2006, vol. 68, Issue 5, pp. 1850-1854 (Abstract Only).
Urashima, Tadasu et al., "Oligosaccharides of Milk and Colstrum in Non-Human Mammals," Glycoconjugate Journal, 2001, vol. 18, pp. 357-371.
Yolken, Robert H. et al., "Antibody to Human Rotavirus in Cow's Milk," The New England Journal of Medicine, 1985, vol. 312, No. 10, pp. 605-610.
Definition of Infant formula, University of Maryland Medical Center, http://umm.edu/health/medical/ency/articles/infant-formulas, dated Sep. 1, 2013.

\* cited by examiner

NUTRITIONAL COMPOSITION COMPRISING INDIGESTIBLE OLIGOSACCHARIDES

FIELD OF THE INVENTION

The present invention provides a method for the prevention and/or treatment of respiratory tract infections, said method comprising the administration of indigestible oligosaccharides.

BACKGROUND OF THE INVENTION

The respiratory tract is a common site for infection by pathogens. It becomes infected frequently because it is in direct contact with the physical environment and is exposed to microorganisms in the air. There are several microorganisms that cause illness in infants.

Respiratory syncytial virus (RSV) is the leading cause of serious lower respiratory tract disease in infants and children. Primary RSV infection occurs most often in children from 6 weeks to 2 years of age. RSV is estimated to cause as much as 75% of all childhood bronchiolitis and up to 40% of all pediatric pneumonias. Children at increased risk from RSV infection include preterm infants and children with bronchopulmonary dysplasia, congenital heart disease, congenital or acquired immunodeficiency and cystic fibrosis The fatality rate in infants with heart or lung disease who are hospitalized with RSV infection is 3%-4%. Treatment options for established RSV disease are limited. Severe RSV disease of the lower respiratory tract often requires considerable supportive care, including administration of humidified oxygen and respiratory assistance.

Parainfluenza viral infection results in serious respiratory tract disease in infants and children. Infectious parainfluenza account for approximately 20% of all hospitalizations of pediatric patients suffering from respiratory tract infections worldwide.

Infants breast fed with mothers milk have a reduced occurrence of respiratory tract infection. In the art, it is presently believed that this reduced occurrence is because mothers milk contains immunoglobulin with virus or other microorganism neutralizing activity.

Treatment of respiratory infection is often difficult. Only a few effective drugs are available and often treatment requires pulmonary administration of the drug. In young infants this leads to significant stress. Therefore there is a need for further effective agents that preferably can be administered without imposing or decreasing imposing stress on infants and children.

Recently is has been described that administration of infant formula enriched with prebiotics (galactooligosaccharides), probiotics, nucleotides and LC-PUFA and with a low level of lactose is useful for infants suffering from respiratory infections (Rivero et al (2004), J Pediatr Gastroenterol Nutr 39: suppl. 1, P1121).

SUMMARY OF THE INVENTION

In a multicentre clinical trial, the present inventors have now surprisingly found that enteral administration of a combination of:
  a) a galactose containing indigestible oligosaccharide containing at least two terminal saccharide units, wherein at least one terminal saccharide unit is selected from the group consisting of glucose and galactose; and at least one terminal saccharide is selected from the group consisting of galactose and fucose; and
  b) a digestible galactose saccharide results in a reduced occurrence of respiratory tract infections, see example 6.

The present method has the advantage that the active principle is safe and can be suitably admixed to nutrition. This leads to significantly reduced stress, particularly in infants. Hence, in one aspect, the present invention comprises the oral administration of a nutritional composition which reduces the occurrence of respiratory tract infection.

The present invention is particularly surprising because until now, it was believe that a low lactose content was essential for the prevention of respiratory disorder in infants. The present inventors found that administering a nutritional composition containing a transgalactooligosaccharide and rich in lactose is particularly effective preventing or treating respiratory infection.

The present inventors have found that both the galactose containing indigestible oligosaccharide and a digestible galactose saccharide are essential for optimal treatment and/or prevention of respiratory infection and/or respiratory infection disease. Moreover, particularly lactose contributes to a reduced occurrence of respiratory tract infection.

Additionally, the present invention is also of significant commercial importance. The manufacture of low lactose formula requires for example the use of a non-milk protein source (e.g. soy protein) or an additional treatment of milk wherein the lactose is removed (e.g. ultrafiltration). Both options are often undesirable as they increase costs and may provide sub-optimal nutrition.

In a further aspect the present invention provides a method for the treatment and/or prevention of respiratory tract infection and respiratory tract infection disease, said method comprising administering a nutritional composition. Administration of the present active principle as a nutritional composition aims to reduce stress and more optimally reduces the occurrence of respiratory infections as said oligosaccharide works synergistically with long chain polyunsaturated fatty acids, the combination of choline and zinc, probiotics and/or prebiotics other than the galactose containing indigestible oligosaccharide. In a preferred embodiment, the present invention provides a method for the treatment and/or prevention of respiratory syncyticial virus infection, said method comprising administrating to an infant with the age between 0 and 2, a nutritional composition comprising an effective amount of transgalactooligosaccharides.

In still a further aspect the present invention provides a composition which is particularly suitable for the treatment and/or prevention of respiratory tract infection and disease, said composition comprising said oligosaccharide and an immunoglobulin with virus neutralizing activity, e.g. immunoglobulin with parainfluenza or RSV neutralizing activity. The immunoglobulin is preferably obtained from a cow hyper-immunised against respiratory virus.

DETAILED DESCRIPTION OF PREFERRED EMBODIMENTS

The present invention provides a method for the treatment and/or prevention of respiratory tract infection and/or respiratory tract infection disease, said method comprising orally administering a composition to a mammal, said composition comprising a galactose-containing indigestible oligosaccharide containing at least two terminal saccharide units, wherein at least one terminal saccharide unit is selected from the group consisting of glucose and galactose; and at least one terminal saccharide is selected from the group consisting of galactose and fucose, and at least 5 wt. % digestible saccharide based on total dry weight of the composition, said saccharide being selected from the group consisting of galactose and digestible galactose containing saccharide containing at least two terminal saccharide units, wherein at least one terminal saccharide unit is selected from the group consisting of glucose and galactose; and at least one terminal saccharide is selected from the group consisting of galactose and fucose.

In a further aspect the present invention provides a composition suitable for the treatment and/or prevention of respiratory tract infections and/or respiratory tract infection disease comprising a. a galactose containing indigestible oligosaccharide containing at least two terminal saccharide units, wherein at least one terminal saccharide unit is selected from the group consisting of glucose and galactose; and at least one terminal saccharide is selected from the group consisting of galactose and fucose;

b. an immunoglobulin having a virus neutralizing effect; and c. a substance of non-human origin.

Optionally this composition further comprises d. at least 5 wt. % digestible galactose saccharide based on total dry weight of the composition, said saccharide being selected from the group consisting of galactose and digestible galactose containing saccharide containing at least two terminal saccharide units, wherein at least one terminal saccharide unit is selected from the group consisting of glucose and galactose; and at least one terminal saccharide is selected from the group consisting of galactose and fucose.

Oligosaccharides

The present invention comprises the administration of a galactose containing indigestible oligosaccharide (GAL-oligo) containing at least two terminal saccharide units, wherein at least one terminal saccharide unit is selected from the group consisting of glucose and galactose; and at least one terminal saccharide is selected from the group consisting of galactose and fucose. Preferably the saccharides of the GAL-oligo are β-linked.

The term "terminal saccharide" refers to a saccharide which is bound to one other saccharide unit (e.g. galactose, glucose, fructose or fucose). The present GAL-oligo preferably contains not more than 4 terminal saccharides, preferably not more than 2. The term "indigestible oligosaccharides" as used in the present invention refers to saccharides which are not or only partially digested in the intestine by the action of acids or digestive enzymes present in the human upper digestive tract (small intestine and stomach) but which are fermented by the human intestinal flora.

In a preferred embodiment, the GAL-oligo contains at least one terminal galactose and one selected from at least terminal glucose and one terminal fucose. Even more preferably, the present galactose containing indigestible oligosaccharide comprises at least one terminal galactose and at least one terminal glucose. Preferably the oligosaccharide consists of 2 terminal saccharide units and 2 to 60 saccharide units in total.

Preferably the GAL-oligo is selected from the group consisting of transgalactooligosaccharides, galactooligosaccharides, lacto-N-tetraose (LNT), lacto-N-neotetraose (neo-LNT), fucosyl-lactose, fucosylated LNT and fucosylated neo-LNT. In a particularly preferred embodiment the present method comprises the administration of transgalactooligosaccharides ([galactose]$_n$-glucose; wherein n is an integer between 1 and 60, i.e. 2, 3, 4, 5, 6, ..., 59, 60; preferably n is selected from 2, 3, 4, 5, 6, 7, 8, 9, or 10). Transgalactooligosaccharides (TOS) are for example sold under the trademark Vivinal™ (Borculo Domo Ingredients, Netherlands). Preferably the saccharides of the transgalactooligosaccharides are β-linked The present composition preferably comprises 0.1 to 12 grams of the GAL-oligo per 100 gram dry weight of the composition, preferably between 0.5 and 8 grams, more preferably between 1.0 and 7.5 grams. After reconstitution of the powder in liquid and administration of the liquid formula to the infant, these amounts of GAL-oligo provide the desired effects without causing intestinal discomfort.

Digestible Galactose Saccharide

The composition used in the present method comprises digestible carbohydrate containing digestible galactose saccharide. The composition contains at least 5 wt. % digestible galactose saccharide based on total dry weight of the composition, said saccharide being selected from the group consisting of galactose and digestible galactose containing saccharide containing at least two terminal saccharide units, wherein at least one terminal saccharide unit is selected from the group consisting of glucose and galactose; and at least one terminal saccharide is selected from the group consisting of galactose and fucose. The composition used in the present method contains at least 5 wt % digestible galactose saccharide based on total dry weight of the present composition, preferably at least 10 wt. %, even more preferably at least 25 wt. %.

The term "digestible galactose saccharide" as used in the present invention refers to mono-, di-, tri- or polysaccharides which are digested in the intestine of normal healthy human by the action of acids or digestive enzymes present in the human upper digestive tract (small intestine and stomach). Preferably lactose is used in the present method.

Preferably the digestible galactose saccharide is lactose. Preferably at least 50 wt % of the carbohydrate of the composition used in the present method is lactose, preferably at least 75 wt. %, even more preferably at least 90 wt. %. The term carbohydrate as used herein refers to digestible carbohydrate, as is common practice. The composition used in the present method preferably contains at least 10 wt % lactose saccharide based on total dry weight of the present composition, preferably at least 25 wt. %, even more preferably at least 40 wt. %, most preferably at least 50 wt. %. In order to provide optimal nutrition to an infant, i.e. a composition which is highly similar to human milk, the present method preferably comprises the administration of a composition comprising between 40 and 60 wt. % lactose based on total dry weight of the composition.

In a further preferred embodiment the present invention relates to the administration of about 2 to 50 grams lactose per serving, preferably about 10 to 25 grams lactose per serving. A serving is preferably between 5 and 500 ml, more preferably between 100 and 300 ml.

The weight ratio digestible galactose saccharide: galactose containing indigestible oligosaccharide is preferably above 1, more preferably above 5, even more preferably above 10. The ratio is preferably below 1000, more preferably below 100.

Combinations of Oligosaccharides

In a particularly preferred embodiment the present method comprises the administration of the present GAL-oligo and an second indigestible oligosaccharides selected from the group consisting of indigestible dextrins, xylooligosaccharides, arabinooligosaccharides, glucooligosaccharides, mannooligo-saccharides, fucooligosaccharides fructans—Levan-type (β-D-(2→6)-fructofuranosyl)$_n$ α-C-D-glucopyranoside) and fructans—Inulin-type (β-D-((2→1)-fructofuranosyl)$_n$ α-D-glucopyranoside). Preferably the second oligosaccharide is selected from the group consisting of inulin, hydrolysed inulin and fructooligosaccharides.

The present composition preferably comprises between 0.5 and 12 grams of the second indigestible oligosaccharide, more preferably between 1 and 8 grams of the second indigestible oligosaccharide per 100 gram dry weight of the present composition. The DP of the second oligosaccharide is preferably below 40, even more preferably between 10 and 30.

Optimally, the present composition comprises between 1 and 12 grams water-soluble indigestible oligosaccharides in total (i.e. with or without a second, third, etc water-soluble indigestible oligosaccharide) per 100 gram dry weight of the present composition, more preferably between 2 and 9 grams in total.

Preferably the weight ratios:
a. (oligosaccharides with DP 2 to 5): (oligosaccharides with DP 6 to 9); and
b. (oligosaccharides with DP 10 to 60): (oligosaccharides with DP 6 to 9) are both above 1.

Preferably both weight ratios are above 2, even more preferably above 5.

The present method preferably comprises the administration of 0.5 to 10 gram transgalactooligosaccharides with DP between 1 and 10 per 100 gram dry weight of the composition, more preferably between 2 and 5 gram. The present invention preferably comprises 0.5 to 10 gram fructopolysaccharide with DP between 15 and 40 per 100 gram dry weight of the composition, more preferably between 1 and 5 gram. The term "fructopolysaccharide" refers to an indigestible polysaccharide carbohydrate comprising a chain of at least 10 β-linked fructose units.

In a further preferred embodiment the second indigestible oligosaccharide is and acid oligosaccharide. The term acid oligosaccharide refers to oligosaccharides comprising at least one acidic group selected from the group consisting of N-acetylneuraminic acid, N-glycoloylneuraminic acid, free or esterified carboxylic acid, sulfuric acid group and phosphoric acid group. The acid oligosaccharide preferably is a polyhexose. Preferably, at least one of the aforementioned acid groups is situated at the terminal hexose unit of the acid oligosaccharide. Preferably the acid oligosaccharide contains a carboxylic acid at the terminal hexose unit, wherein said carboxylic acid group may be free or esterified. Methods for the manufacture of esterified pectin hydrolysates that can be suitably used in the present method and composition are provided in WO 01/60378 and/or WO02/42484, which are hereby incorporated by reference.

Preferably, the acid oligosaccharide has one, preferably two, terminal uronic acid units, which may be free or esterified. Preferably the terminal uronic acid unit is selected from the group consisting of galacturonic acid, glucuronic acid, guluronic acid, iduronic acid, mannuronic acid, riburonic acid and alturonic acid. These units may be free or esterified. In an even more preferred embodiment, the terminal hexose unit has a double bond, which is preferably situated between the $C_4$ and $C_5$ position of the terminal hexose unit. Preferably one of the terminal hexose units comprises the double bond. The terminal hexose (e.g. uronic acid) preferably has a structure according to Figure 1.

Figure 1: Preferred Terminal Hexose Acid Group

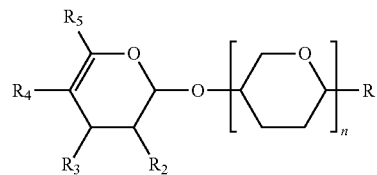

wherein;
R is preferably selected from the group consisting of hydrogen, hydroxy or acid group, preferably hydroxy (see above); and
at least one selected from the group consisting of $R_2$, $R_3$, $R_4$ and $R_5$ represents N-acetylneuraminic acid, N-glycoloylneuraminic acid, free or esterified carboxylic acid, sulfuric acid group and phosphoric acid group, and the remaining of $R_2$, $R_3$, $R_4$ and $R_5$ representing hydroxy and/or hydrogen. Preferably one selected from the group consisting of $R_2$, $R_3$, $R_4$ and $R_5$ represents N-acetylneuraminic acid, N-glycoloylneuraminic acid, free or esterified carboxylic acid, sulfuric acid group and phosphoric acid group, and the remaining of $R_2$, $R_3$, $R_4$ and $R_5$ represent hydroxy and/or hydrogen. Even more preferably one selected from the group consisting of $R_2$, $R_3$, $R_4$ and $R_5$ represents free or esterified carboxylic acid and the remaining of $R_2$, $R_3$, $R_4$ and $R_5$ represent hydroxy and/or hydrogen; and n is an integer and refers to a number of hexose units (see also Degree of Polymerisation, below), which may be any hexose unit. Suitably n is an integer between 1-5000 representing the number of hexose units said hexose units preferably being uronic acid, even more preferably being galacturonic acid units. The carboxylic acid groups on these units may be free or (partly) esterified, and are preferably at least partly methylated.

Most preferably, $R_2$ and $R_3$ represent hydroxy, $R_4$ represent hydrogen and $R_5$ represents free or esterified carboxylic acid.

The acid oligosaccharide as used in the present method, has a degree of polymerisation (DP) between 1 and 5000, preferably between 1 and 1000, more preferably between 2 and 250, even more preferably between 2 and 50, most preferably between 2 and 10. If a mixture of acid oligosaccharides with different degrees of polymerisation is used, the average DP of the acid oligosaccharide mixture is preferably between 2 and 1000, more preferably between 3 and 250, even more preferably between 3 and 50.

The acid oligosaccharides are preferably characterised by a degree of methoxylation above 20%, preferably above 50% even more preferably above 70%. Preferably the acid oligosaccharides have a degree of methylation above 20%, preferably above 50% even more preferably above 70%.

The acid oligosaccharide is preferably administered in an amount of between 10 mg and 100 gram per day, preferably between 100 mg and 50 grams per day, even more between 0.5 and 20 gram per day.

Respiratory Tract Infection

The present invention provides a method for the treatment and/or prevention of respiratory tract infection, which is typically caused by bacterial, viral or fungal infection. In a preferred embodiment the present method provides a method for the treatment and/or prevention of respiratory tract infection caused by *Pneumococcus, Legionella, Streptococcus, Pseudomonas, Staphylococcus*, Heamofilis, *Mycoplasma*, Mycobacteria, *Chlamidia, Moraxella, Coxiella, Nocardia, Klebsiella, Enterobacter, Proteus, Serratia, Acinetobacter*, Orthomyxovirida, Myxovirus, Orthomyxokvirus, Rhinovirus, Echoviruses, Coxsackieviruses, Adenovirus, Parainfluenzavirus, Respiratory Syncytial virus (RSV), Coronavirus, Measles virus, Cytomegalovirus, *Histoplasma capsulatum, Coccidioides immitis, Blastomyces dermatitidis, Cryptococcus Aspergillus*, Mucorales. The present method is particularly suitable for the treatment and/or prevention of respiratory syncytial virus infection.

In a preferred embodiment, the present method relates to the treatment and/or prevention of respiratory tract infection disease, preferably selected from the group consisting of tuberculosis, bronchitis, bronciolitis, tracheitis, pneumonia, sinusinitis, rhinitis, severe acute respiratory syndrome (SARS), croup epiglottitis, histoplasmosis, coccidioidomycosis, blastomycosis, cryptococcosis, aspergillosis, mucormycosis and lung abcess. In a particularly preferred embodiment the invention provides a method for the treatment and/or prevention of viral pneumonia and/or bronchitis.

The present method is also suitable for the treatment and/or prevention of symptoms of respiratory tract infection selected from the group consisting of irritation in the lungs, congestion in the lungs, excessive mucus production, breathlessness (i.e. difficulty with breathing), particularly breathlessness.

Treatment Group

The present method is particularly suitable for treatment and/or prevention of respiratory infections in children with the age between 0 and 10 years, preferably infants with the age between 0 and 4 years. The present method can advantageously be used for the treatment and/or prevention of the above mentioned disease, infection and symptoms in premature infants (an infant born before 37 weeks gestation).

The present method is particularly suitable for the treatment and/or prevention of respiratory infections in immunocompromised mammalian subjects, preferably elderly (human above the age of about 60), subjects infected with human immunodeficiency virus (HIV), subjects suffering from one or more of the following diseases: nephrotic syndrome, multiple myeloma, lymphoma, Hodgkin's disease, subjects which have undergone organ transplantation, subjects with chronic illnesses of the hart, kidney or lungs (especially chronic obstructive pulmonary disease (COPD), lung emphysema, sarcoidosis, cystic fybrosis, bronchiectasis, lung cancer, atelectasis, respiratory failure, occupational lung diseases, asthma), diabetes and alcoholism. The present method is advantageously used for the treatment and/or prevention of patients with COPD, HIV infection and/or diabetes, as these patients are often weakened by the disease.

In a further preferred embodiment, the present method comprises the administration of the present composition to humans, mostly hospitalized patients, that are on a ventilator or artificial breathing machine, or in the intensive care unit, as these patients are particularly vulnerable for viral infections.

Nutritional Formula

Drug treatment of respiratory tract infection in infants with the age between 0 and 4 is often cumbersome because many of the medicaments have to be administered via the pulmonary route. The present invention provides a method for treatment and/or prevention of respiratory infections comprising orally administering a nutritional composition. Hence, the present method also overcomes the problem of pulmonary administration.

The nutritional composition suitable for use in the present method preferably contains between 10 and 60 en % lipid, between 5 and 50 en % protein, between 15 and 90 en % carbohydrate. More preferably the nutritional composition contains between 7.5 to 12.5 energy % protein; 40 to 55 energy % carbohydrates; and 35 to 50 energy % fat. (en % is short for energy percentage and represents the relative amount each constituent contributes to the total caloric value of the preparation).

The nutritional composition preferably also contains at least one long chain polyunsaturated fatty acid (LC-PUFA) preferably selected from the group consisting of eicosapentaenoic acid (EPA, n-3), docosahexaenoic acid (DHA, n-3) and arachidonic acid (AA, n-6), as these further reduce the respiratory tract infections and/or symptoms thereof. Preferably the present composition contains AA and DHA, even more preferably AA, DHA and EPA. The present combination of indigestible oligosaccharide(s) and LC-PUFA acts synergistically.

Preferably the present composition comprises at least 0.1 wt. %, preferably at least 0.25 wt %, more preferably at least 0.5 wt. %, even more preferably at least 0.75 wt. % LC-PUFA with 20 and 22 carbon atoms of the total fat content. The content of LC-PUFA with 20 and 22 carbon atoms in the present composition, preferably does not exceed 15 wt. % of the total fat content, preferably does not exceed 10 wt. %, even more preferably does not exceed 5 wt. % of the total fat content.

The EPA content preferably does not exceed 15 wt. % of the total fat, more preferably does not exceed 5 wt. %, most preferably does not exceed 1 wt. %, but is preferably at least 0.05 wt %, more preferably at least 0.1 wt. % of the total fat. The DHA content preferably does not exceed 10 wt. %, more preferably does not exceed 5 wt. %, most preferably does not exceed 1 wt. %, but is at least 0.1 wt % of the total fat. The present composition preferably comprises at least 0.1 wt. % AA, even more preferably at least 0.25 wt. % AA, most preferably at least 0.5 wt. % AA based on total fat. The AA content preferably does not exceed 5 wt. %, more preferably does not exceed 1 wt. % of the total fat.

Composition suitable for administration to adults may comprise increased amounts of LC-PUFA. The EPA content in this case preferably does not exceed 15 wt. % of the total fat, more preferably does not exceed 10 wt. %, but is preferably at least 0.05 wt %, more preferably at least 0.1 wt. % of the total fat. The DHA content preferably does not exceed 15 wt. %, more preferably does not exceed 10 wt. %, but is at least 0.1 wt % of the total fat. The present composition preferably comprises at least 0.1 wt. % AA, even more preferably at least 0.25 wt. % AA, most preferably at least 0.5 wt. % AA based on total fat. The AA content preferably does not exceed 15 wt. %, more preferably does not exceed 10 wt. % of the total fat.

The present method does not include a method comprising the administration of a composition consisting of human milk. Hence, preferably the present method includes the administration of a composition comprising a substance of non-human origin which is preferably a nutritional substance suitable for oral administration to a human, more preferably a fiber carbohydrate, fat and/or protein of non-human origin, preferably from plant, animal, bacterial or synthetic origin.

Immunoglobulin

The present invention also provides for a composition which is particularly suitable for use in a method for the treatment and/or prevention of respiratory tract infection, said composition comprising the above described indigestible oligosaccharide(s) and an immunoglobulin having a virus neutralizing effect, preferably an immunoglobulin capable of neutralizing a virus selected from the group consisting of Myxovirus, Orthomyxokvirus, Rhinovirus, Echoviruses, Coxsackieviruses, Adenovirus, Respiratory Syncytial virus (RSV), Coronavirus, Measles virus and Cytomegalovirus. The immunoglobulin preferably is IgA and/or IgG, and preferably is obtained from a hyperimmunised mammal, preferably a cow. Methods for obtaining these immunoglobulins from a hyperimmunised mammal are well known to the skilled man and are for example described in GB1573995.

The hyperimmunised mammal is preferably immunised with an antigen capable of stimulating the production of immunoglobulins with virus neutralising activity, said virus being selected from the group of Myxovirus, Orthomyxokvirus, Rhinovirus, Echoviruses, Coxsackieviruses, Adenovirus, Respiratory Syncytial virus (RSV), Coronavirus, Measles virus and Cytomegalovirus. In a particularly preferred embodiment the present composition comprises an immunoglobulin with RSV neutralizing activity.

The present composition does not include a composition consisting of human milk. Hence, preferably the present composition comprises a substance of non-human origin, preferably a nutritional substance, more preferably from plant, animal, bacterial or synthetic origin. The substance is preferably a fiber, carbohydrate, fat or protein.

The present composition is also advantageously combined with at least one selected from the group consisting of LC-PUFA (as described above), digestible galactose saccharide (see above), probiotics (as described below), choline (see below) and zinc (see below).

Probiotics

In a further preferred embodiment, the present method comprises the administration of the above-described indigestible oligosaccharide(s) and a probiotic. Preferably the probiotic is selected from the group Lactobacillus, Lactococcus, Bifidobacterium, Enterococcus, Propionibacterium, Pediococcus, Bacillus and *Streptococcus* and more preferably from the group consisting of Lactobacillus and Bifidobacterium. The probiotic is preferably a non-pathogenic lactic acid-producing bacterium. The combination of the present indigestible oligosaccharide(s) and the probiotic bacteria acts synergistically.

Choline and Zinc

In a further preferred embodiment, the present composition includes zinc and/or choline. Both zinc and choline stimulate the formation of healthy lung tissue membranes, and thereby result in an improved resistance to infection. Compositions including zinc and/or choline can advantageously be used in the present method. The present composition preferably contains between 5 and 500 mg choline per 100 gram dry weight of the composition, more preferably between 20 and 100 mg choline, even more preferably between 40 and 60 mg choline. The present composition preferably contains between 1 and 100 mg zinc per 100 gram dry weight of the composition, more preferably between 2 and 50 mg zinc, even more preferably between 10 and 25 mg zinc.

EXAMPLES

Example 1

| Packaged infant milk formula provided with a label indicating that the formula can be suitably used to prevent respiratory tract infection by respiratory syncytial virus formula containing per 100 ml final product (and per 13.1 g powder): | |
|---|---|
| 8 energy % protein | 1.4 g (casein whey mixture) |
| 45 energy % digestible carbohydrates | 7.5 g |
| 47 energy % fat | 3.5 g |
| transgalactooligosaccharides (TOS) | 0.3 g |

Example 2

Packaged infant milk formula according to example 1, wherein the packaging is provided with a label indicating that the formula can be suitably used to reduce difficulty with breathing.

Example 3

| Packaged infant milk formula according to example 1, further containing per 100 ml final product (and per 13.1 g powder); | |
|---|---|
| Raftilin HP, Orafti BE) | 0.1 g |
| *Bifidobacterium breve*: | $1.3 \times 10^8$ cfu |
| tuna fish oil | 0.3 gram |
| 40% arachidonic acid oil | 0.3 gram |
| (DSM Food Specialties, Delft, Netherlands) | |

Example 4

| Packaged infant milk formula according to example 3, further containing per 100 ml final product (and per 13.1 g powder); | |
|---|---|
| choline | 6.5 mg |
| zinc | 2 mg |

Example 5

Packaged infant milk formula according to example 1, further containing immunoglobulin with respiratory syncytial virus neutralizing activity as described in EP0808173.

Example 6

Effectiveness of transgalactooligsaccharides in standard infant formula's for prevention of respiratory tract infections in infants of the age until 1 year.

Method: A multicentre clinical trial was performed in Italy, including 7 centers and 56 paediatricians. At the moment breast-feeding was stopped, infants were divided into two groups. The infants in Group A (n=69) were administered Nutrilon™ 1 or 2 supplemented with oligosaccharides to a final concentration of 0.36 g transgalactooligosaccharides/100 ml (Vivinal-GOS™; Borculo Domo Ingredients, Netherlands) and 0.04 g fructopolysaccharide/100 ml (Raftiline HP™, Orafti, Tienen, Belgium). The infants in control group B (n=82) received standard Nutrilon™ 1 or 2. Nutrilon 1™ contains 45 en % carbohydrate, 8 en % protein and 47 en % fat; about 97 wt % lactose based on total carbohydrate; 7.3 gram lactose per 100 ml; about 54 gram lactose per 100 gram dry weight of the complete composition.

Nutrilon 2™ contains 47 en % carbohydrate, 10 en % protein and 43 en % fat; about 96 wt % lactose based on total carbohydrate; 7.9 gram lactose per 100 ml; about 54 gram lactose per 100 gram dry weight of the complete composition.

Results: The age of the infants varied between 2 and 9 months and the infants were followed for 6 months. Both groups did not show any difference in nutritional intake. In group A a total number of 32 upper respiratory tract infection episodes was observed. In control group B a total number of 60 upper respiratory tract infection episodes was observed. Thus the incidence of upper respiratory infection episodes was significant (p<0,01) lower in group A vs group B.

Example 7

Sachet

Sachet containing 1 gram lactose and 0.5 gram transgalactooligosaccharides, for addition to a liquid nutrition containing fat, protein and carbohydrate designed for ingestion by patients suffering from COPD or diabetes, said sachet being provided with a label indicating that addition of the contents of the sachet to the nutrition reduces the incidence of respiratory tract infection development.

The invention claimed is:

1. A method for reducing the occurrence of respiratory tract infections in a human infant between 0 and 2 years of age suffering from respiratory tract infections, said method comprising orally administering to the infant an infant formula composition free of human milk comprising:
  (a) 0.1 to 12 grams indigestible galacto-oligosaccharides per 100 gram dry weight of the composition; and
  (b) at least 5 weight % based on total dry weight of the composition of a digestible galactose saccharide, said saccharide being selected from the group consisting of galactose and digestible galactose having at least two terminal saccharide units, wherein one terminal saccharide unit is glucose or galactose, and the other terminal saccharide is galactose or fucose,
  wherein the infant formula composition does not comprise a probiotic.

2. The method according to claim 1, wherein the respiratory tract infection is a respiratory syncytial virus infection, childhood bronchiolitis and/or pediatric pneumonia.

3. The method according to claim 1, wherein the treatment is for childhood bronchiolitis, pediatric pneumonia, or both.

4. The method according to claim 1, wherein the human infant was born preterm or suffers from bronchopulmonary dysplasia, congenital heart disease, congenital or acquired immune deficiency syndrome, cystic fibrosis, chronic obstructive pulmonary disease, or diabetes.

5. The method according to claim 1, wherein the galactose-oligosaccharides are transgalactooligosaccharides with a degree of polymerisation between 2 and 10.

6. The method according to claim 1, wherein the composition further comprises a second indigestible oligosaccharide selected from the group consisting of fructooligosaccharides, hydrolysed inulin, and inulin.

7. The method according to claim 1, wherein the composition further comprises a fat, carbohydrate, protein, or combinations thereof.

8. The method according to claim 7, wherein the fat is a long chain polyunsaturated fatty acid selected from the group consisting of eicosapentaenoic acid, docosahexaenoic acid, and arachidonic acid.

9. The method according to claim 7, wherein the fat, carbohydrate, or protein is of plant, non-human animal, bacterial, or synthetic origin.

10. The method according to claim 7, comprising between 10 and 60 energy % fat, between 15 and 90 energy % carbohydrate, and between 5 and 50 energy % protein.

11. The method according to claim 1, wherein the composition further comprises probiotic bacteria.

12. The method according to claim 11, wherein the probiotic bacteria is *Lactobacillus, Bifidobacterium, Lactococcus, Pediococcus, Enterococcus, Propionibacterium, Bacillus, Streptococcus*, and combinations thereof.

13. The method according to claim 1, wherein the composition further comprises acid oligosaccharides.

14. The method according to claim 1, wherein the composition does not comprise an immunoglobulin having respiratory syncytial virus neutralizing activity.

15. The method according to claim 2, wherein the composition comprises 0.1 to 12 grams of the transgalactooligosaccharides per 100 gram dry weight of the composition, and further comprises:
  a. between 10 and 60 energy % lipid; between 5 and 50 energy % protein; and between 15 and 90 energy % carbohydrate;
  b. between 40 and 60 weight % lactose based on total dry weight of the composition; and
  c. at least one of eicosapentaenoic acid, docosahexaenoic acid, or arachidonic acid.

16. The method according to claim 1, wherein the respiratory tract infection is an upper respiratory tract infection.

17. The method according to claim 1, wherein the digestible galactose saccharide (b) is lactose.

18. A method for reducing the occurrence of respiratory tract infections in a human infant between 0 and 2 years of age suffering from respiratory tract infections, said method comprising orally administering to the infant an infant formula composition free of human milk and comprising:
  (a) indigestible transgalactooligosaccharides with a degree of polymerisation between 2 and 10; and
  (b) at least 5 weight % based on total dry weight of the composition of a digestible galactose saccharide, said saccharide being selected from the group consisting of galactose and digestible galactose having at least two terminal saccharide units, wherein one terminal saccharide unit is glucose or galactose, and the other terminal saccharide is galactose or fucose,
  wherein the composition does not comprise a probiotic.

19. The method according to claim 18, wherein the respiratory tract infection is a respiratory syncytial virus infection, childhood bronchiolitis and/or pediatric pneumonia.

20. The method according to claim 18, wherein the composition further comprises a second indigestible oligosaccharide selected from the group consisting of fructooligosaccharides, hydrolysed inulin, and inulin.

21. The method according to claim 18, wherein the composition does not comprise an immunoglobulin having respiratory syncytial virus neutralizing activity.

* * * * *